(12) United States Patent
Somani et al.

(10) Patent No.: US 9,339,186 B2
(45) Date of Patent: May 17, 2016

(54) METHOD AND APPARATUS FOR ENHANCED EYE MEASUREMENTS

(75) Inventors: Seema Somani, Karnataka (IN); Jay Wei, Fremont, CA (US)

(73) Assignee: Optovue, Inc., Fremont, CA (US)

( * ) Notice: Subject to any disclaimer, the term of this patent is extended or adjusted under 35 U.S.C. 154(b) by 0 days.

(21) Appl. No.: 13/150,999

(22) Filed: Jun. 1, 2011

(65) Prior Publication Data

US 2011/0292341 A1   Dec. 1, 2011

Related U.S. Application Data

(60) Provisional application No. 61/350,258, filed on Jun. 1, 2010.

(51) Int. Cl.
| A61B 3/14 | (2006.01) |
| A61B 3/10 | (2006.01) |
| A61B 3/15 | (2006.01) |

(52) U.S. Cl.
CPC ....................................... *A61B 3/152* (2013.01)

(58) Field of Classification Search
USPC ......... 351/200, 201, 203, 205, 206, 208, 210, 351/211, 222, 221
See application file for complete search history.

(56) References Cited

U.S. PATENT DOCUMENTS

| 5,493,109 | A | 2/1996 | Wei et al. | |
| 6,485,413 | B1 | 11/2002 | Boppart et al. | |
| 7,497,575 | B2 * | 3/2009 | Huang et al. | 351/206 |
| 2004/0066489 | A1 | 4/2004 | Benedikt et al. | |
| 2005/0041210 | A1 | 2/2005 | Isogai et al. | |
| 2007/0076219 | A1 * | 4/2007 | Toida | 356/511 |
| 2007/0291277 | A1 * | 12/2007 | Everett et al. | 356/497 |
| 2008/0013093 | A1 * | 1/2008 | Izatt et al. | 356/456 |
| 2008/0100612 | A1 | 5/2008 | Dastmalchi et al. | |
| 2008/0304144 | A1 * | 12/2008 | Reimer | A61B 5/0066 359/377 |
| 2009/0046250 | A1 * | 2/2009 | Mattioli et al. | 351/212 |
| 2009/0079993 | A1 * | 3/2009 | Yatagai et al. | 356/497 |
| 2009/0161090 | A1 * | 6/2009 | Campbell et al. | 356/3 |
| 2009/0180123 | A1 | 7/2009 | Knighton et al. | |
| 2009/0257065 | A1 | 10/2009 | Hauger et al. | |
| 2010/0103374 | A1 | 4/2010 | Hirose et al. | |
| 2011/0080561 | A1 * | 4/2011 | Hayashi et al. | 351/206 |

FOREIGN PATENT DOCUMENTS

| CN | 101072534 A | 11/2007 |
| CN | 101405562 A | 4/2009 |

(Continued)

OTHER PUBLICATIONS

ISR and Written Opinion for related PCT Application No. PCT/US2011/038809, dated Sep. 27, 2011.

(Continued)

*Primary Examiner* — Joseph P Martinez
*Assistant Examiner* — Brandi Thomas
(74) *Attorney, Agent, or Firm* — Haynes & Boone, LLP

(57) ABSTRACT

An imaging method according to some embodiments of the present invention includes obtaining working distance information from an optical coherence tomography system, the working distance being the working distance to the sample; obtaining information from one or more ocular systems; combining the information from said optical coherence tomography information and said ocular system; and displaying said combined information.

8 Claims, 9 Drawing Sheets

(56) References Cited

FOREIGN PATENT DOCUMENTS

| | | | | |
|---|---|---|---|---|
| EP | 1939579 A2 | 7/2008 | | |
| JP | 2002-529184 A | 9/2002 | | |
| JP | 2005052249 | 3/2005 | | |
| JP | 2007-181631 | * 7/2007 | ............... | A61B 3/14 |
| JP | 2007/181631 A | 7/2007 | | |
| JP | 2008154941 | 7/2008 | | |
| JP | 2009-230141 A | 10/2009 | | |

OTHER PUBLICATIONS

PCT International Preliminary Report on Patentability mailed Dec. 13, 2012, in related International Application No. PCT/US2011/038809.

Office Action mailed Dec. 22, 2014, in related Chinese Application No. 201180032685.2.

Office Action (Notice of Reasons for Rejection) mailed Oct. 14, 2014, in related Japanese Application No. 2013-513329.

* cited by examiner

METHOD AND APPARATUS FOR ENHANCED EYE MEASUREMENTS

RELATED APPLICATIONS

This application claims priority to U.S. Provisional Application 61/350,258, filed on Jun. 1, 2010, which is herein incorporated by reference in its entirety.

BACKGROUND

1. Field of Invention

The embodiments described herein relate generally to methods and systems for collecting and processing images in ophthalmology.

2. Background State of the Art

To acquire accurate and repeatable images and measurements of a subject eye, it is desirable to image the subject eye at a fixed distance and at a reproducible location from the imaging device. Therefore, it is important to identify the desirable working distance (also known as the Z distance) between the subject eye and the imaging device. A shift in the position from this fixed distance could lead to inaccurate and less reproducible images, or even errors in measurements.

Corneal topography, for example, is an imaging modality where acquiring accurate and repeatable images is important. Corneal topography uses a method called reflective projection. In this method, a desirable light pattern is projected onto the front surface of a subject eye. A virtual image of the light pattern is then formed near the cornea and captured by an imaging device inside the corneal topographer. The spatial information from this virtual image of the light pattern near the cornea provides information to generate the topographical images of the subject eye. The resulting topographical images are highly sensitive to the distance between the subject eye and the corneal topographer. Since cornea is a high optical power surface, a small variation from a fixed distance between the subject eye and the imaging device can introduce significant measurement errors. If the eye is moved away from the fixed distance at the focal point, the magnification of the virtual image would change and thus result in error of the topographic images or measurements.

Several approaches have been attempted to reduce the error by imaging the subject eye in a fixed position or a more reproducible distance. There are three main approaches, namely 1) reference imaging method, 2) beam triangulation based method and 3) maximum signal method.

FIG. 1 shows an example of the reference imaging method attempting to achieve a reliable fixed distance with a light source 104 and placido object 102 as discussed, for example, in U.S. Pat. No. 5,847,804. The method illustrated in FIG. 1 uses one or more additional imaging device(s) 106 placed off of the optical axis of a main imaging device 108. The distance from the cornea of the subject eye 110 to the main imaging device 108 is determined from the images acquired by the additional imaging device(s) 106. For example, in FIG. 1, additional cameras 106 are placed at a distance perpendicular to the optical axis of the main imaging device 108. An operator then adjusts the distance between the main imaging device 108 and the subject eye 110 until the video image of the eye 110 in additional imaging devices 106 reaches a certain location. This location is identified as the fixed location and images are taken on main imaging device 108 at this location. However, the reference imaging method is highly subjective and difficult to perform for different face sizes and profiles. The desirable fixed location cannot be achieved with high accuracy and repeatability using such method.

FIG. 2 shows an example of the triangulation based method as discussed, for example, in U.S. Pat. No. 6,450,641. Two or more light beams 204 from light sources 202 are used to set a distance of the cornea 208 from the imaging device (not shown). Focusing aid light beams 204 of the imaging device travel at a set angle from the optical axis 206 of the imaging device and are oriented in such a way that the reflected beams 204 either intersect or focus a pattern at a desired distance from the imaging device to achieve the fixed distance. In some examples, an operator of the imaging device is required to adjust the imaging device during an eye exam to locate the intersection of beams 204 reflected from the cornea surface of the subject eye. In another implementation, an operator adjusts the imaging device to position and align a light pattern on the sclera or limbus area of the subject eye as a focusing aid. This triangulation beam method again is subject dependent and presents difficulties for the operator to locate the beam intersection on the cornea. This approach can be uncomfortable for a patient who is subjected to exposure of the multiple aiming beams and is also not user friendly due to the added complexity of additional light beams.

Another method utilized in the attempt to solve the positioning problem is the maximum signal method. In this method, either an aiming light or the main instrument light reflected from the eye is analyzed. In one implementation, the total reflected light reflected from the eye is maximized at a point to achieve best working distance for the subject eye. The distance to achieve maximum reflected light is used as the desired working distance for the main imaging instrument. In another implementation, a series of images are taken during acquisition. Then, the image with the highest signal and/or sharpness is identified and used as the best image for measurement and analysis, without evaluating the proper working distance. These methods and other similar variations are widely practiced in many commercial imaging instruments and cameras. However, these methods are not very reliable because there are other factors affecting the quality and signal of the acquired images such as ambient light.

Thus there is a need for better systems to acquire images of the eye.

SUMMARY

In accordance with some embodiments of the present invention, an imaging apparatus includes an optical coherence tomography (OCT) system, one or more ocular systems, and a coupler coupled to the optical coherence tomography system and the one or more ocular systems, wherein the coupler provides a combination beam.

An imaging method according to some embodiments of the present invention includes obtaining working distance information from an optical coherence tomography system, the working distance being the working distance to the sample; obtaining information from one or more ocular systems; combining the information from said optical coherence tomography information and said ocular system; and displaying said combined information.

These and other embodiments are further described below with respect to the following figures.

Where appropriate, elements having the same or similar functions have the same element designation. Figures are not to scale and do not illustrate relative sizes.

DETAILED DESCRIPTION

In accordance with some embodiments of the present invention, a method and an apparatus of determining an accurate and more reproducible position between a sample object and an imaging or measurement device is disclosed. Some embodiments below disclose methods and apparatus to enhance image reproducibility and accuracy of imaging instruments such as, for example, a topography system by incorporating an Optical Coherence Tomography (OCT) measurement. OCT is a very precise technique commonly used for imaging and measuring 3-D structure of biological tissue, for example, the human eye. The OCT technique can be applied together with other imaging systems to provide additional valuable information not available in the individual imaging systems to correlate, register and enhance the measurements and analysis. For example, a precise working distance between the subject eye and the imaging system can be determined by incorporating the OCT technique so that the eye can be placed at an optimal position for accurate and reproducible imaging and measurement. OCT is well-known to produce high resolution images and this high resolution produces extremely accurate distance measurement. Combining OCT technology with other ocular systems/applications is advantageous to provide a precise working distance and accurate positioning of the subject eye relative to the ocular system/application. OCT can be combined with several other ocular applications, for example topography system, keratometry system, fundus imaging system, wavefront system, biometry measurement system and laser surgery system.

Figure 1:
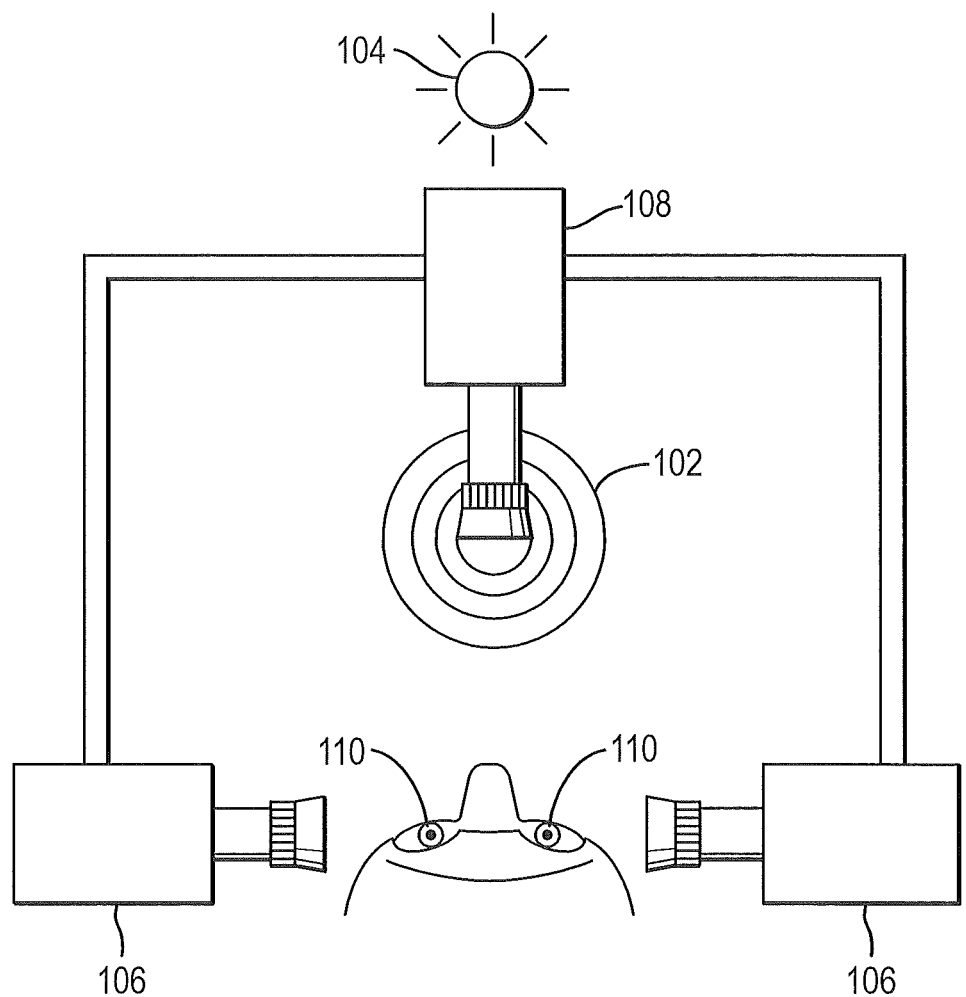
FIG. 1 shows an example of Z distance assessment using reference imaging method through side view cameras.
Figure 2:
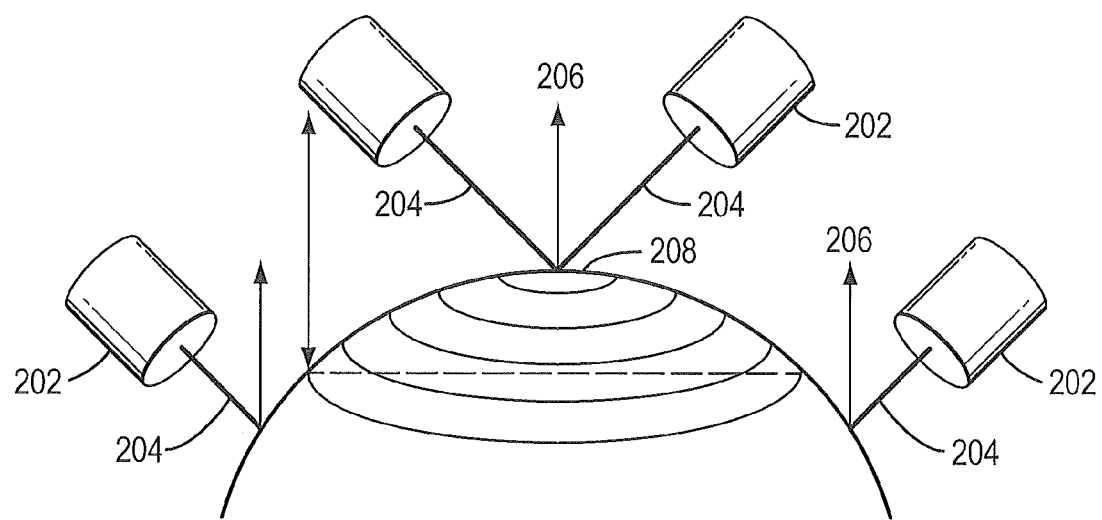
FIG. 2 shows an example of Z distance assessment using a beam triangulation method with multiple light beams incident upon the eye.
Figure 3:
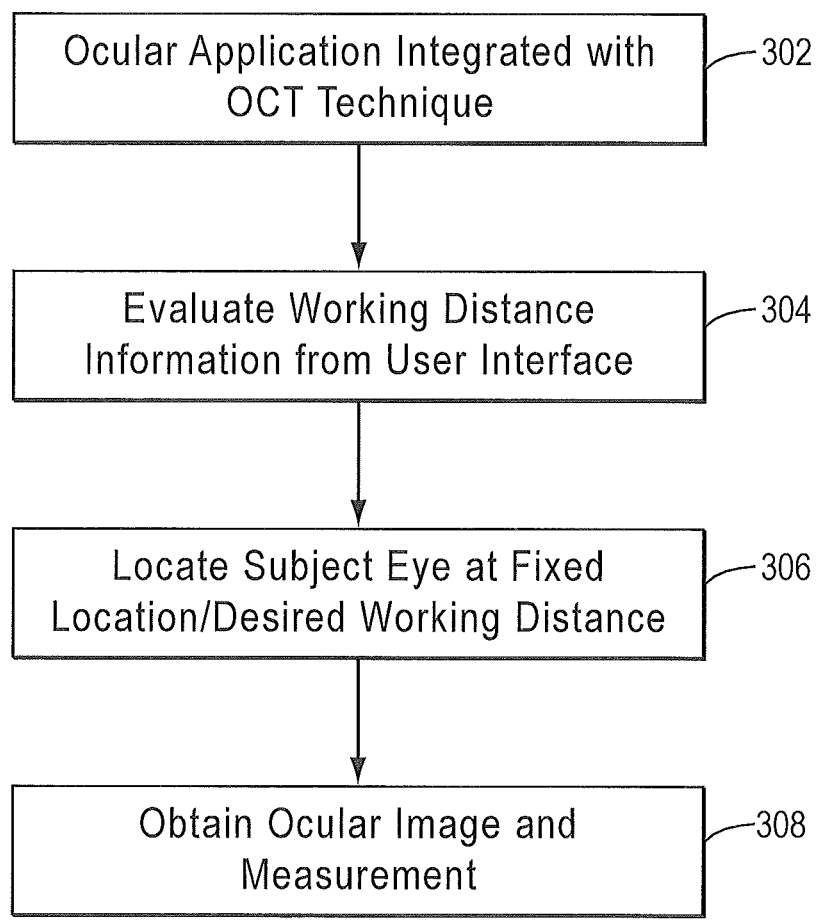
FIG. 3 shows an exemplary flow diagram in accordance with some embodiments of the present invention.

FIG. 3 shows an exemplary flow diagram of a method to precisely manage the working distance for ocular applications in accordance with some embodiments of the present invention. In the example illustrated in FIG. 3, the OCT technique is used in combination with an ocular application such as topography imaging. A topography imager provides topography information of the front of the subject eye and an OCT system generates precise 3D intensity data corresponding to an axial reflection distribution arising from reflecting features in the eye. The topographic information and the OCT information are commonly used by doctors and clinicians to view and diagnose various pathologies in patient's eye. An example of a topography system in combination with an OCT system is further discussed below.

Figure 4:
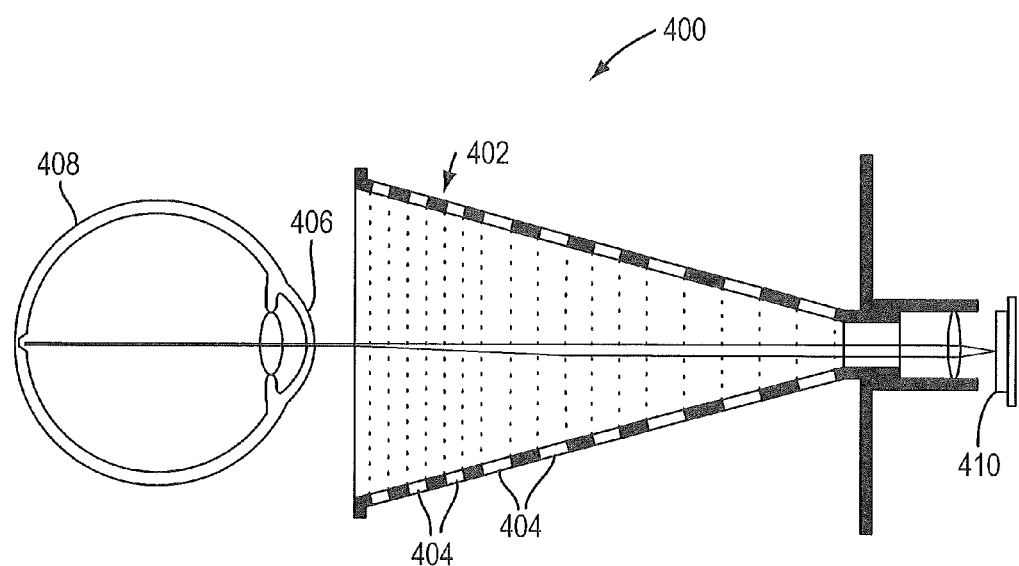
FIG. 4 shows a schematic diagram of a topography system that can be used in some embodiments of the present invention.
Figure 5:
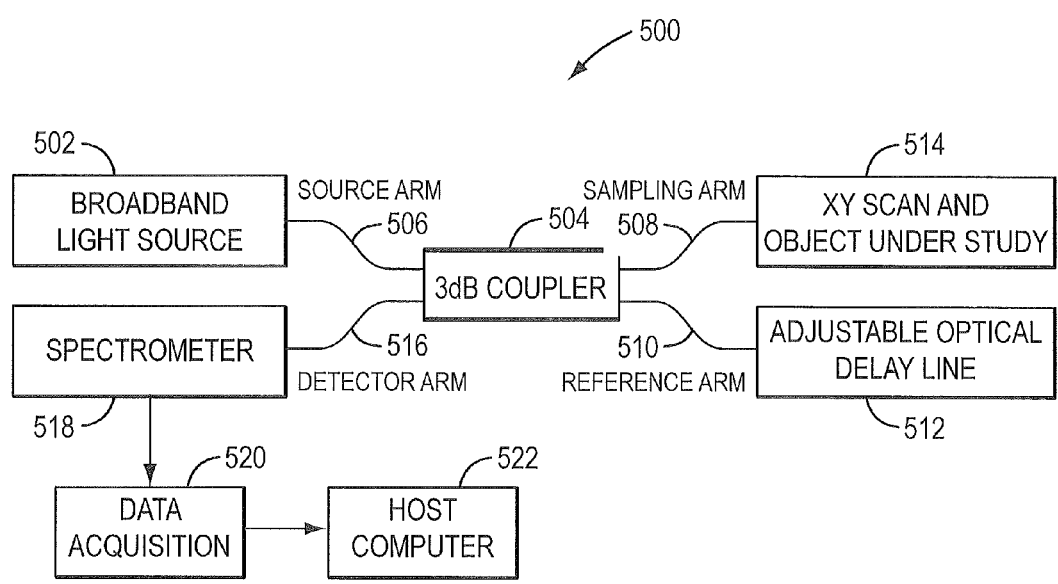
FIG. 5 shows a schematic diagram of an OCT system that can be used in some embodiments of the present invention.

In step 302 shown in FIG. 3, one or more ocular applications are integrated into an OCT system. In some embodiments, a topography imager is integrated with an OCT system. A topography imager is a commonly used imaging device to provide topographical information of an eye. FIG. 4, which is discussed in more detail below, illustrates an example of a topography system and its related optical components that can be utilized in some embodiments of the present invention. An OCT system is also a commonly used imaging device to provide high-speed, high resolution 3D images and measurements of an eye. FIG. 5, which is discussed in more detail below, illustrates an OCT system and its related optical components that can be utilized in some embodiments of the present invention.

In step 304 of FIG. 3, the OCT information and the information of the selected ocular application(s) can be displayed or evaluated to achieve a desired working distance for optimized imaging. In step 306, the integrated imaging system or the subject eye can be positioned to obtain the desired information from the ocular application. In some embodiments, the positioning process of step 306 can be automated for ease of use and to further reduce the subjectivity of operator manipulations. Once the position of the working distance is determined, the ocular image and/or measurement can then be obtained in step 308.

FIG. 4 shows a schematic diagram of a topography system 400 and related optical components that can be incorporated in some embodiments of the present invention. As shown in FIG. 4, system 400 includes a cone surface 402 on which lies a set of concentric rings pattern 404, called placido rings. Rings 404 can be illuminated by an illumination circuit. The front part 406 of the eye 408 acts as a reflector for this ring light pattern from rings 404. A virtual image of the ring source is formed slightly behind the front surface of the eye 408. This image is relayed by imaging optics to a camera 410 placed on the optical axis and through a hole in the cone of rings 404. The size and the magnification of the rings 404 are related to the optical power reflected from the reflector, in this case, the cornea of the subject eye 408. Using system 400, the image of rings 404 can then be analyzed to estimate the optical power and subsequently the curvature profile of the cornea of subject eye 408.

Due to the lack of control of the working distance and/or the inability to reproducibly acquire information of subject eye 408 at a fixed location at a desired distance, measurement errors are likely to be introduced. The measurement errors at issue with topography system 400, the inability in capturing reproducible and accurate topographic information, are illustrated in FIG. 6.

Figure 6:
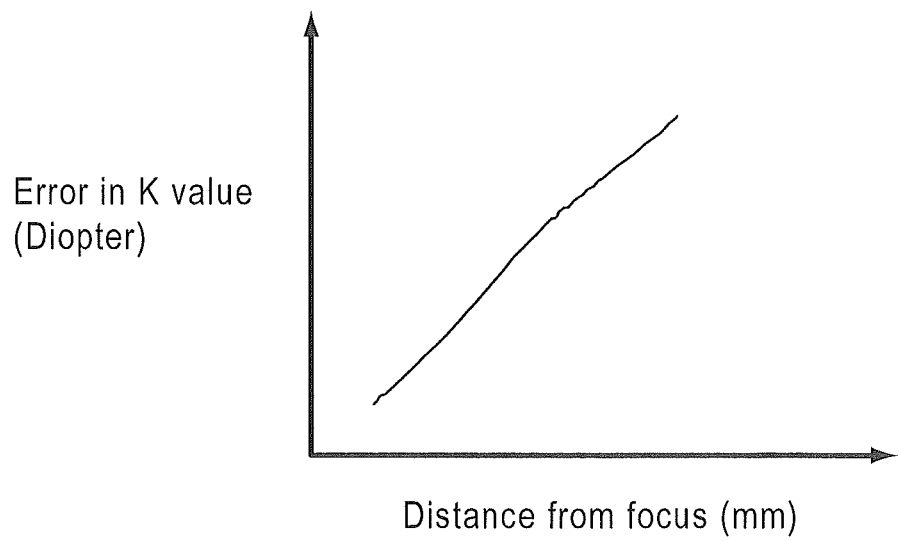
FIG. 6 shows an illustrative plot showing the relationship between measurement error and working distance.

As shown in FIG. 6, measurement error of the optical power of the cornea is related to the working distance. The optical power of the cornea is also known as the K (keratometry) values. The K values are calculated by the magnification of the image of the ring/annular (placido) light source. As shown in FIG. 6, the image magnification changes with the change in the distance between the object and the imager, in this case the ring-light-to-eye distances. As illustrated in FIG. 6, the measured values are only correct at the origin and the error in K value increases as the distance from the optimal focus increases.

FIG. 5 shows a schematic diagram of an OCT system 500 and related optical components that can be incorporated in the present invention according to some embodiments. In a Fourier Domain OCT (FD-OCT) system a broadband light source 502 is coupled into a 4 port fiber coupler 504. Light from the source 502 travels through fiber 506 and is split into two fibers 508 and 510. Fiber 508 sends light through a 2-dimensional (X-Y) scanning optics and object under study 514. The light reflected by the different tissues and structures in the object, which may be an eye, retraces the same path and is coupled into the fiber 508. The fiber 510 carries the light to a reference path 512. The reference path can, for example, be an adjustable delay line. The optical length of the fiber 510 plus path 512 should match with fiber 508 plus path 514 within the coherence length of the source in order to create an interference of the two paths.

Light from fibers 508 and 510 is combined together by coupler 504 and coupled into fiber 516. A spectrometer 518 receives the light from fiber 516 and spreads the light on to a linear detector or line camera. The signal from the line camera is captured by data acquisition electronics 520 and sent to host computer 522 for processing. The computer 522 performs the inverse Fourier transforms of the intensity signal and generates depth information and/or images.

In addition, the Fourier-domain OCT system can be based on a spectrometer, as discussed above, or based on a rapidly tuned laser (also known as "swept source"). In some embodiments, the wavelength or frequency of a laser is swept over a range supported by the laser's gain medium. The light reflected during a wavelength sweep can be collected with a single photodetector, instead of spectrometer 518.

Figure 7:
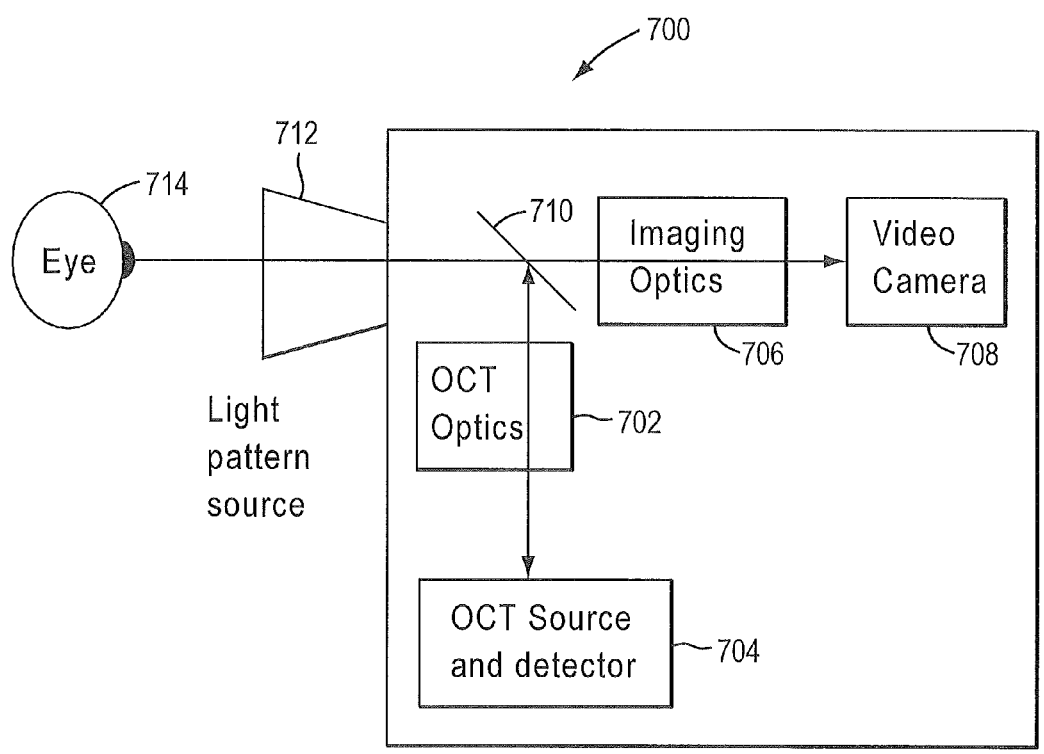
FIG. 7 shows an exemplary schematic diagram of a combined OCT and topography system according to some embodiments of the present invention.

FIG. 7 is an exemplary schematic diagram of a combined OCT and topography system 700 according to some embodiments of the present invention. System 700 allows operators to obtain the precise distance of the region of interest of the eye for image acquisition and allows the subject eye to be placed at exact focus for the topography system with no or minimum magnification error. For example, the region of interest can be the anterior segment or the posterior segment of the subject eye. In the combined system in FIG. 7, the OCT optical path 702 and 704 and the imaging path of the topography system 706 and 708 are combined together through a beam splitter 710. A placido cone 712 is mounted at the front of the combined system 700. From the OCT path 702, a light beam is sent to the eye 714 and scanned over the region of interest to obtain OCT information, such as depth or image information of the eye. The imaging optics 706 and video camera 708 optical path obtains the image of the placido cone 712 projected onto the eye. In this manner, the magnification power of the cornea, in this example, can be calculated using the information from the placido cone of the topography system at a known and well defined distance using the depth information from the OCT system. The interference signal of the OCT system gives the position of the eye relative to a reference position. The relative distance between the eye and system 700 can then be varied until it reaches the desired position, such as the apex of the cornea.

In some embodiments, the imaging optics module 706 can include a set of lenses used to relay the virtual image of the ring light pattern formed by cornea to an imaging detector, as shown in FIG. 4. In another aspect, the video camera (imaging detector) module 708 can be a CCD or a CMOS camera. In another aspect, the OCT source and detector module 704 can be a near infrared SLD (super luminescence diode). This SLD may have a bandwidth of 40 nm or wider to achieve fine spatial resolution. The OCT detector of the OCT source and detector module 704 can be a spectrometer composed of collimation lens(s), a holographic diffraction grating and CCD or CMOS line camera.

In some embodiments, a time-domain OCT system can be used to deliver the precise working distance with the integrated system 700 in FIG. 7. Preferably, spectral or Fourier domain OCT can be used; a Fourier domain OCT system has the advantage of being significantly faster than the time-domain OCT counterpart with improved imaging resolution. This faster scan rate of the Fourier domain OCT can further eliminate the error due to eye motion during acquisition because of the reduction in acquisition time.

Figure 8:
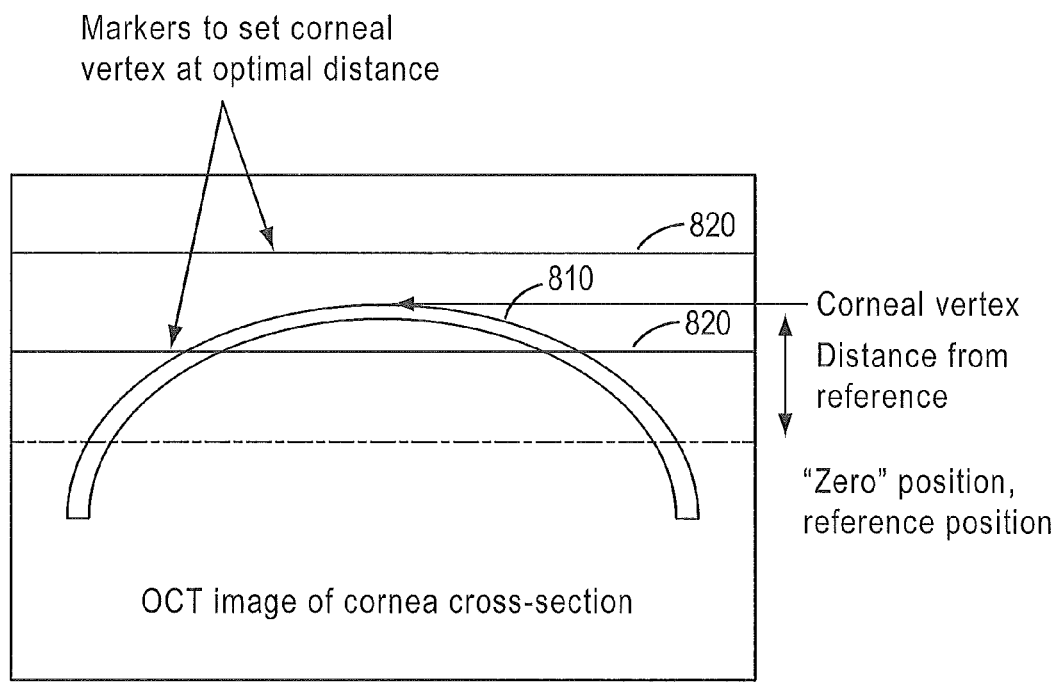
FIG. 8 is an exemplary user interface for high precise placement of the subject eye.

FIG. 8 illustrates an exemplary user interface display with information for the distance measurement position method. In FIG. 8, an OCT image 810 of the frontal portion of the eye, such as the cornea, is displayed along with two horizontal guidelines on a user interface. An operator can adjust the X-Y position of this image to properly align the eye. The OCT image 810 shows the precise distance of the eye real-time during acquisition as shown in FIG. 8. To achieve best working distance to image the cornea surface, for example, a user can bring the apex of the cornea (corneal vertex) between the two guideline markers 820. The distance between the two guideline markers 820 can be adjusted depending on the desired precision of the working distance determination of the eye. A smaller distance between the marker lines 820 will result in a more precise positioning of the corneal apex, while a larger distance will allow more tolerance in positioning. In some embodiments, three horizontal guidelines, two guidelines 820 and a target line, can be displayed with the OCT image in an application user interface. In this example, the user can achieve precise positioning of corneal apex by bringing the apex of cornea as close to the target line as possible while staying within the range of the two guideline markers 820. When the apex of the cornea is located at the target line, the distance of the cornea to the instrument can be set very accurately at the desired distance, which can be adjusted by modifying the position of the target line.

In some embodiments, this manual alignment process can be automated to enhance ease of use and further reduce subjectivity of positioning placement by an operator. For example, a motorized system can be implemented to provide automatic adjustment of the working distance between the sample and the imager. The motorized system can be an XYZ table that provides automatic movement in the X, Y, and/or Z direction. Additionally, rotational motorized system can also be used to reduce error in distance due to rotation of the subject eye. The working distance information captured in this integrated system 700 can be evaluated to automatically place the object of interest in the desired location. For example, the apex of the cornea can be automatically placed at the target line or in the middle of the guidelines 820 as in FIG. 8.

In addition to improving the measurement accuracy and reproducibility of the topography measurement by combining OCT technology and topography, the synergy of these two modalities further allows the OCT data to be correlated with image data obtained from topography system. The coordinates of the common image features of these two imaging modalities using a system in FIG. 7 can be related by coordinate transformation such that OCT data can be registered with topography data. In some embodiments, OCT technology can be combined with wavefront measurements. OCT technology, as discussed above, provides image and measurement of the structure of an object of interest. On the other hand, wavefront technology provides measurements of visual function, such as visual acuity, of the eye. Such combination of OCT and wavefront technologies can allow effective imaging, measurement and presentation of the structural information from OCT and the functional information from wavefront of the subject eye. Common features of regions of interested acquired from different modalities can be further manipulated and registered to enhance measurement understanding, including registration of measurement results, from the combined modalities.

Figure 9:
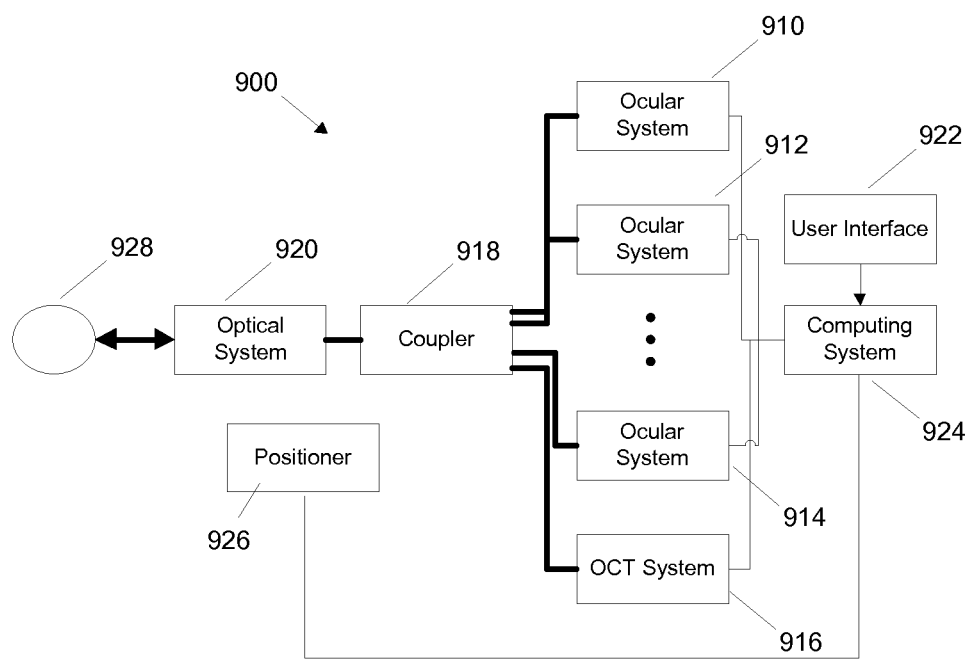
FIG. 9 illustrates an example system according to some embodiments of the present invention.

FIG. 9 illustrates a system 900 according to some embodiments of the present invention. As shown in FIG. 9, one or more ocular systems or ocular applications such as systems 910, 912, and 914 are optically coupled to a coupler 918. There may be any number of ocular systems 910, 912, and 914 coupled into coupler 918. Ocular systems 910, 912, and 914 can be any optical imaging systems or ocular applications, for example a topography system, keratometry system, fundus imaging system, wavefront system, biometry system, or a laser surgery system. System 900 also includes an OCT system 916 coupled to coupler 918. Coupler 918 can be any device or combination of devices that combine multiple beams of light into a single beam of light and that couples a beam of light reflected from sample 928 into each of the respective ocular systems 910, 912, and 914 as well as OCT system 916.

The combined optical output from coupler 918 is coupled into optical system 920, which directs light onto sample 928, such as an eye as shown in FIG. 9. Optical system 920 can be any device or combination of devices that allow the beam from coupler 918 to be coupled to sample 928 and which couples light from sample 928 back to coupler 918. Optical system 920 can also be one or more light sources such as placido cone 712 shown in FIG. 7.

Light from sample 928 is then coupled through optical system 920 and coupler 918 into the respective imaging systems 910, 912, 914 and OCT system 916. Each of imaging systems 910, 912, 914 and 916 analyze the optical light from sample 928 and provides electrical signals to computing system 924. Computing system 924 can be any computing device capable of analyzing data from ocular systems 910, 912, 914, and OCT system 916. Computing system 924 analyzes the information and images formed from each of systems 910, 912, 914, and 916. As discussed above, information and images obtained from these systems can be correlated, registered and referenced from and against each other. Further, computing system is coupled to a user interface 922, which can be any combination of user input and display devices. User interface 922, for example, can be utilized to display the interface image shown in FIG. 8.

In some embodiments, OCT system 916 provides positioning information between sample 928 and optical system 920 to user interface 922. As discussed in FIG. 7 above, for example, imaging system 910 can be a topographic imaging system and optical system 920 can be a placido cone to obtain topographic information of the eye, with working distance accurately and repeatably determined by the information obtained using the OCT system 916. In some embodiments, the positioning information can be supplied to a positioner 926. Positioner 926 adjusts the distance between sample 928 and system 900 according to the positioning information supplied. In some embodiments, positioner 926 can adjust components in optical system 920. In some embodiments, all of system 900 may be moved to adjust the distance based on the positioning information supplied. In some embodiments, the positioner 926 can adjust the position of sample 928 relative to system 900 to achieve the best focus and best working distance.

The above examples are provided in order to demonstrate and further illustrate certain embodiments and aspects of the present invention and are not to be construed as limiting the scope thereof. In the description above, reference is made primarily to the eye as the object. This has to be understood as merely a way to help the description and not as a restriction of the application of the present invention. As such, where the term "eye" is used, a more general transparent and scattering object or organ may be sought instead. Although various embodiments that incorporate the teachings of the present invention have been illustrated and described in detail herein, a person of ordinary skill in the art can readily device other various embodiments that incorporate the teachings of this subject invention.

We claim:

1. An imaging apparatus, comprising:
    an optical coherence tomography (OCT) system;
    one or more ocular systems;
    a coupler coupled to the OCT system and the one or more ocular systems; and
    an optical system coupled to the coupler, the optical system coupling a combination beam from the coupler to a sample, and light reflected from the sample to the coupler,
    wherein the coupler is configured for providing the combination beam from the OCT system and the one or more ocular systems to the optical system, and the reflected light from the optical system to the OCT system and the one or more ocular systems, and
    wherein the OCT system is configured to use an interference signal of the OCT system to determine a current working distance (Z distance) between the optical system and the sample and provide positioning information to a positioner coupled to the optical system for positioning the optical system such that the current working distance determined by the OCT system matches a desired working distance of the one or more ocular systems.

2. The apparatus of claim 1, wherein the one or more ocular systems includes at least one of a set consisting of a topography system, a keratometry system, a fundus imaging system, a wavefront system, a biometry system, and a laser surgery system.

3. The apparatus of claim 1, wherein said coupler includes at least one beam splitter.

4. The apparatus of claim 1, further including a computing system coupled to the one or more ocular systems, wherein the computing system is configured for analyzing information from the OCT system and providing the positioning information to a display.

5. The apparatus of claim 4, wherein the positioner is configured to adjust a position of the one or more ocular and the OCT systems relative to the sample.

6. The apparatus of claim 1, wherein the one or more ocular systems includes a topography imager.

7. The apparatus of claim 1, wherein the optical system includes a placido cone.

8. The apparatus of claim 1, wherein the OCT system includes a time-domain OCT system, a spectrometer based frequency-domain OCT system, and a swept-source based frequency-domain OCT system.

* * * * *